(12) United States Patent
Schmenger et al.

(10) Patent No.: US 8,398,724 B2
(45) Date of Patent: Mar. 19, 2013

(54) METHODS FOR PREPARING HAIR COLORING COMPOSITIONS

(75) Inventors: Juergen Schmenger, Weiterstadt (DE); Manfred Schmitt, Bensheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/352,552

(22) Filed: Jan. 18, 2012

(65) Prior Publication Data

US 2012/0180230 A1 Jul. 19, 2012

(30) Foreign Application Priority Data

Jan. 18, 2011 (EP) .................................... 11151283

(51) Int. Cl.
*A61Q 5/10* (2006.01)
(52) U.S. Cl. .............. 8/405; 8/406; 8/431; 8/435; 8/594
(58) Field of Classification Search ............. 8/405, 406, 8/431, 435, 594
See application file for complete search history.

(56) References Cited

U.S. PATENT DOCUMENTS

| | | | |
|---|---|---|---|
| 5,480,459 A | 1/1996 | Mager | |
| 6,146,429 A | 11/2000 | Gast | |
| 6,423,101 B1 * | 7/2002 | Yaker et al. ........................ | 8/405 |
| 7,186,275 B2 | 3/2007 | Boswell | |
| 2006/0248661 A1 | 11/2006 | Wood | |
| 2008/0052841 A1 | 3/2008 | Cohen | |
| 2008/0222820 A1 | 9/2008 | Siracusa | |
| 2009/0158533 A1 | 6/2009 | Hercouet | |
| 2009/0162309 A1 | 6/2009 | Hercouet | |
| 2009/0191142 A1 | 7/2009 | Hercouet | |
| 2010/0154136 A1 | 6/2010 | Hercouet | |
| 2010/0154137 A1 | 6/2010 | Hercouet | |
| 2010/0154140 A1 | 6/2010 | Simonet | |
| 2010/0154141 A1 | 6/2010 | Hercouet | |
| 2010/0154142 A1 | 6/2010 | Audousset | |
| 2010/0162492 A1 | 7/2010 | Hercouet | |
| 2010/0162493 A1 | 7/2010 | Audousset | |
| 2010/0166688 A1 | 7/2010 | Hercouet | |
| 2010/0175202 A1 | 7/2010 | Simonet | |
| 2010/0175203 A1 | 7/2010 | Audousset | |
| 2010/0175705 A1 | 7/2010 | Hercouet | |
| 2010/0175706 A1 | 7/2010 | Hercouet | |
| 2010/0178264 A1 | 7/2010 | Hercouet | |
| 2010/0186177 A1 | 7/2010 | Hercouet | |
| 2010/0199441 A1 | 8/2010 | Hercouet | |
| 2010/0223739 A1 | 9/2010 | Hercouet | |
| 2010/0247465 A1 | 9/2010 | Simonet | |
| 2011/0232667 A1 | 9/2011 | Hercouet | |
| 2012/0180231 A1 | 7/2012 | Schmenger | |

FOREIGN PATENT DOCUMENTS

| | | |
|---|---|---|
| EP | 1568354 A1 | 8/2005 |
| FR | 2925308 B1 | 12/2009 |
| FR | 2940056 A1 | 6/2010 |
| FR | 2940052 B1 | 2/2011 |
| FR | 2940076 B1 | 3/2011 |
| GB | 1271331 A | 4/1972 |
| GB | 2358643 A | 8/2001 |
| JP | 2010077084 | 4/2010 |

\* cited by examiner

*Primary Examiner* — Eisa Elhilo
(74) *Attorney, Agent, or Firm* — James T. Fondriest; Carl J. Roof

(57) ABSTRACT

Methods for providing, at the discretion of the user, at least two different oxidative hair coloring compositions providing different level of lift based on a single tint component. The methods involve the use of a tint component, an oxidizing component and a third component comprising a non-ammonia alkalizing agent. The compositions may comprise little or no ammonia.

17 Claims, No Drawings

METHODS FOR PREPARING HAIR COLORING COMPOSITIONS

FIELD OF THE INVENTION

The invention relates to methods for making oxidative hair coloring composition having relatively high lift. In addition to the usual tint component and oxidizing component, the method involves mixing a third component comprising a non-ammonia alkalizing agent. The invention may be used for making, at the discretion of the user, two or more different oxidative hair coloring compositions providing different level of lift based on a single tint component by adding or not the third component. The user, which may be a professional hair stylist, is thus provided with a versatile system for preparing for example a first hair coloring composition having a relatively lower lift or a second hair coloring composition having a relatively higher lift compared to the first hair coloring composition. The compositions obtained by the method of the invention and the components used in the invention may comprise little or no ammonia.

BACKGROUND OF THE INVENTION

Two-component permanent oxidative hair colorants comprising a tint component and an oxidizing component are commonly used in professional hair salons. The tint component contains so-called oxidative primary dyes which are small molecules (primary intermediates or couplers) and an alkalizing agent, usually ammonia. These primary dyes react with each other in the presence of an oxidizing agent to form larger, colored molecules. The tint component is thus mixed with the oxidizing component immediately prior to application to the hair to be colored and the resulting mixture is applied on hair for 10 to 50 mn usually for 15 to 35 mn. The oxidizing component may be for example a diluted stabilized solution of hydrogen peroxide. The mixture usually has an alkaline pH of between about 9.5 and 10.5.

Because the primary dyes are small enough to migrate into the hair shaft but the resulting colored molecules are too large to easily leave the hair, the resulting coloration is stable and undergo little fading. Furthermore, hydrogen peroxide, especially in the presence of ammonia, is capable of bleaching melanin, so that it is possible to obtain shades which are lighter or darker than the natural colour. Thus oxidative dye compositions comprising ammonia as alkalizing agent are often referred to as permanent hair colorants or "Level 3" hair colorant. Permanent hair colorants are for example marketed under the Koleston Perfect brand name by Wella Professional in Europe.

Demi-permanent hair colorants, also referred to as "level 2" colorants, are also two-component systems. They use primary dyes as in permanent hair colorants but differ in that they use other alkalizing agents than ammonia, in particular alkanolamines such as monoethanolamine (MEA) or aminomethylpropanol (AMP), and usually lower concentration of hydrogen peroxide (1 to 3 weight % (w. %) in the mixed product ("on-head" composition) compared to 3 to 6 w. % for permanent dyes). Other peroxides may also be used for Level 3 bleaching composition, e.g. persulfate, as oxidizing agent. Demi-permanent hair colorants usually provoke less melanin bleaching and thus less lift (i.e. removal) of natural hair color. The resulting dyes also penetrate less deeply in the hair shaft so that demi-permanent hair colorants can be less stable than permanent hair colorants. On the other hand, demi-permanent hair colorants are usually also less damaging to the hair structure than permanent hair colorants and the resulting hair color may also be more natural looking. Demi-permanent hair colorant compositions do not have the strong ammonia smell of permanent hair colorant and thus have a better consumer acceptance. A professional brand of demi-permanent dyes in Europe is for example Color Touch from Wella Professional.

Some oxidative colorant products sometimes referred to as lightening or bleaching products comprise little amount of precursor dyes (one can set an arbitrary limit at less than 0.3% by weight of precursor dyes of the composition on-head). For such products, the color change therefore mainly results in the degradation of the natural melanin of hair by the oxidizing agent in an alkaline environment.

Ammonia-free hair coloring products have been proposed with the goal to provide coloring results close to those obtained with permanent dyes containing ammonia. For example Schwarzkopf has launched in 2009 in Germany a two-component ammonia-free colorant product under the brand name Essensity. The alkalizing agent used is MEA and relatively high level of hydrogen peroxide is used (up to 7.7% on head).

U.S. Pat. No. 6,423,101, assigned to EUGENE PERMA discloses an ammonia-free composition for dyeing keratinous fibers, comprising an oxidant compound, coloring agent precursors and a non-volatile odorless alkalizing agent characterized in that it further comprises: a quaternized copolymer of dimethyldiallyl ammonium and acrylic acid; a quaternized silicone; an acrylic-itaconic copolymer esterified with one or several fatty alcohol's, optionally polyoxyethylenated. The composition is prepared using a two-component system with MEA as alkalizing agent. According to this Patent, the specific ternary complex claimed provides coloration which gives good coverage and resistance similar to coloration using ammonia.

US2010/0154141A1 assigned to L'Oreal discloses a process for coloring keratin materials comprising: applying to said keratin materials a coloring composition comprising a direct emulsion (A) comprising at least one fatty substance other than fatty acids present in an amount greater than 25% by weight; at least one surfactant; at least one alkaline agent; at least one colored or coloring entity chosen from direct dyes and oxidation dyes; and water in an amount greater than 5% by weight relative to the total weight of the direct emulsion (A); and a composition (B) comprising at least one oxidizing agent. The alkanolamine is preferably chosen from 2-amino-2-methyl-1-propanol and monoethanolamine.

Although hair coloring products obtained by mixing two components are most commonly used, products obtained by mixing three components have also been disclosed. US2008/0052841A1 assigned to LES PRODUITS VERNICO LTEE for example discloses a method for permanently modifying a color of keratinous fibers with a mixture of three compositions A, B and C, wherein said composition A comprises at least a reducing agent and optionally a coloring compound, said composition B comprises at least an alkalizing compound and said composition C comprises at least an oxidizing compound.

US2010/0223739A2 assigned to L'Oreal discloses a process and kit for dyeing keratin fibers, in which the following are applied to the fibers: an aqueous cosmetic composition (A) comprising at least one fatty substance and at least one surfactant; a cosmetic composition (B) comprising at least one alkaline agent, a cosmetic composition (C) comprising at least one oxidizing agent, wherein the amount of the at least one fatty substance in composition (A) is greater than 20% by weight relative to the total weight of composition (A), and when the process used is a process for dyeing keratin fibers, then cosmetic composition (B) further comprises at least one oxidation dye, at least one direct dye, or both.

Further patent applications assigned to L'Oreal disclose coloring compositions obtained by mixing three components. For example US2009/0191142 discloses a process for dyeing human keratin fibers in the presence of at least one oxidizing agent, comprising applying to the fibers at least one anhydrous composition (A) comprising at least one fatty substance and at least one surfactant, at least one composition (B) comprising at least one oxidizing agent, and at least one composition (C) comprising at least one dye chosen from direct and oxidation dyes, and at least one organic amine having a pKb at 25° C. of less than 12. The disclosure also relates to a multi-compartment device containing, in separate compartments, the compositions (A), (B), and (C); and a method of making a ready-to-use composition. The present disclosure also relates to an anhydrous composition comprising at least one fatty substance, at least one surfactant, at least one dye, and at least one organic amine. L'Oreal's US2009/0162309, US2009/0158533, US2010/0175705, US2010/0175706, US2010/0178264, US2010/0154137 also disclose three-component coloring compositions.

In addition, L'Oreal has launched in 2009 in Western Europe a three-component system for professional usage under the brand name INOA. The INOA products comprise a fatty component, a concentrated dye component and an oxidizing component to be mixed immediately before use. The fatty component comprises primarily mineral oil and does not comprise an alkalizing agent. The dye component comprises MEA as alkalizing agent. The 3 components are recommended to be mixed in a 40:16:60 weight ratio.

Although the prior art discloses using two or three components to obtain a permanent hair color result without ammonia, the prior art has not provided a versatile system for providing different level of lift and/or intensity of color at the discretion of the user based a single tint component.

Furthermore Level 2 and Level 3 products, even provided by the same company, usually are based on very different chassis. For example, although the INOA products from L'Oreal achieve or are close to achieve level 3 results without ammonia, they require the use of high level of a fatty phase and have a completely different formulation than other L'Oreal's Level 2 products. This increases complexity and costs.

The present inventors have now surprisingly found that it was possible to increase the lift provided by non-ammonia based oxidative two-component colorant products by mixing them with a third component. The third component comprises a non-alkalizing agent. It was surprisingly found that for example a conventional Level 2 product may achieve a lift up to a classic Level 3 product with the adjunction of the third alkalizing component.

It was also surprisingly found that the color shift in the three-component system of the invention relative to the two-component system was not significant. Thus the user can add the third component of the invention to a two-component based composition, in order to provide a composition having higher lift while achieving the same tonality. A further advantage is thus that existing two-component "Level 2" coloring products can be "boosted" into "Level 3" coloring products by the addition of this third component, thus extending the range of results achievable at very little cost and complexity.

Thus, the present invention provides a simple and cost-efficient system for providing at the choice of the user a first or a second coloring compositions having relatively less or relatively more lift based on the same tint component.

SUMMARY OF THE INVENTION

In a first aspect, the inventive is for a method for making an oxidative hair coloring composition. The method comprises the steps of providing a tint component and an oxidizing component and then mixing the tint component and the oxidizing component with a third component comprising a second non-ammonia alkalizing agent to make the oxidative hair coloring composition. The tint component comprises a first non-ammonia alkalizing agent and oxidative primary dyes. The third component was found to be able to raise the lift of the oxidative coloring composition.

In a second aspect, the invention is for a method for making at the discretion of the user either a first oxidative hair coloring composition or a second oxidative hair coloring composition having a relatively higher lift than said first oxidative hair coloring composition, based on the same tint component comprising a first non-ammonia alkalizing agent and oxidative primary dyes. The method comprises the steps of:

mixing the tint component with a first oxidizing component to obtain the first hair coloring composition; or providing a third component comprising a second non-ammonia alkalizing agent; and mixing the tint component with a second oxidizing component and the third component to obtain a second hair coloring composition having a relatively higher lift than the first coloring composition.

The second oxidizing component may be the same as or different than the first oxidizing component. The second non-ammonia alkalizing agent may be the same as or different than the first non-ammonia alkalizing agent.

This and other features of the methods according to the present invention are further disclosed in the following description and claims.

DETAILED DESCRIPTION OF THE INVENTION

Definitions

By "oxidative hair coloring composition", it is meant a ready-to-use composition which can change the color of hair on which it is applied and which comprises an alkalizing agent, an oxidizing agent and oxidative primary dyes. By "two-component" oxidative hair coloring composition it is meant an oxidative hair coloring composition which is obtained by mixing shortly before use two components: a tint component and an oxidizing component. The tint component comprises the oxidative primary dyes and the alkalizing agent. The oxidizing component comprises the oxidizing agent. By "component" it is meant an individual composition which is mixed by the user with one or more other components for preparing the ready-to-use composition to be applied to the hair. By "user" it is meant the person preparing the hair coloring composition. The user may be for example a professional hair stylist working in a salon and thus a different person than the one on which hair the composition is applied, or the user may be the same person as the one to which the hair belongs.

By "lift" (or "lift power") it is meant the amount of removal of the natural hair pigment that the coloring composition can provide. The amount of lift provided by different hair coloring compositions can be compared using human natural dark hair sample (e.g. hair of individual of Chinese descent) and measuring the change of color achieved following application of the compositions. The change in color can be measured using well known parameters such as L*a*b* values. A composition can be said to provide a higher lift than another composition when the ΔL* value measured for a given treated sample of dark hair is higher for that composition than for the other composition, using the same experimental condition of course. The denomination Level 2 (herein used interchangeably with "demi-permanent" or "tone-on-tone") and Level 3 (herein used interchangeably with "permanent") are commonly used in the hair care trade to differentiate compositions with medium and high lift, although there is no official definition for differentiating a Level 2 from a Level 3.

By "oxidizing agent" it is meant an electron accepting compound suitable for use in hair coloring compositions for removing the natural color of hair (by destroying the melanin pigment) and reacting with oxidative primary dyes to provide an oxidative hair color. The most commonly used oxidizing agent in the art is hydrogen peroxide, however further suitable oxidizing agents that can be used alone or in combination with hydrogen peroxide will be described below.

By "alkalizing agent" it is meant one or more compound suitable for raising the pH to alkaline level in hair coloring compositions, in particular to a pH between 9 and 11. Generally, the most commonly used alkalizing agent in the art is ammonia, however the present invention involves using alkalizing agent other than ammonia (herein "non-ammonia" alkalizing agent), in particular alkanolamines such as monoethanolamine. Alternative non-ammonia alkalizing agents will be described below.

Herein, "comprising" means that other steps and other ingredients can be added to the term qualified. On the other hand, the term "consisting of" means that other steps and other ingredients (other than trace amount) are excluded.

All percentages are by weight of the ready-to-use coloring composition (i.e. as applied on head after the two or more components have been mixed) unless specifically stated otherwise. All ratios are weight ratios unless specifically stated otherwise.

Introduction

In a first aspect, the present invention is for a method for making a oxidative hair coloring composition. The coloring composition can be based on a two-component oxidative coloring composition which can be obtained by mixing a tint component which comprises a first non-ammonia alkalizing agent and oxidative primary dyes and an oxidizing component. The method comprises the step of mixing the tint component and the oxidizing component with a third component comprising a second non-ammonia alkalizing agent. The third compound was found to be able to increase the lift of the coloring composition compared to two-component composition without the third component.

The inventors have indeed surprisingly found that it was possible to raise the lift of a standard coloring two-component composition by providing a third component comprising a second non-ammonia alkalizing agent to be mixed with the two other components. The third component may be based on a similar chassis as the tint component to ease mixing but this is not required. For example, the tint component and third component may be oil-in-water emulsion. The second non-ammonia alkalizing agent may be the same or different than the first non-ammonia alkalizing agent.

The tint and oxidative components may be for example the components of an already marketed oxidative two-component demi-permanent coloring composition ("level 2") for which it is desired to achieve a level of lift equal to or comparable to a permanent coloring composition ("level 3").

The inventors have found that the invention in a second aspect can be used to provide at the discretion of the user two different oxidative hair coloring compositions having different lifts based on a single tint component which is a tint component comprising a first non-ammonia alkalizing agent and oxidative primary dyes. This method comprises the steps of:

mixing the tint component with a first oxidizing component to obtain a first hair coloring composition; or providing a third component comprising a second non-ammonia alkalizing agent; and mixing the tint component with a second oxidizing component and the third component to obtain a second hair coloring composition having a relatively higher lift than the first coloring composition.

Without wishing to be bound by theory, the inventors believe that the third component raises the relative concentration of non-ammonia alkalizing agent in the mixed composition compared to the composition without the third component. Until the invention, it was generally thought that the lift power of a composition was driven by the concentration of oxidizing agent. However, it is also known that raising the concentration of oxidizing agent on-head can also increase the damage caused to the structure of hair fiber. The inventors now believe that it is in fact possible to increase the lift power of a composition by increasing the relative concentration of non-ammonia alkalizing agent relative to the concentration of oxidizing agent. In addition, the inventors have found that damages are kept in this way at relatively low level, and that for coloring composition the rise of the alkalizing agent concentration in the composition does not cause substantial color shift.

The different components may be in any usual cosmetic form, in particular oil-in-water emulsion. The oxidizing component may also be an oil-in-water emulsion or in other form for example a powder or an aqueous solution.

Non-Ammonia Alkalizing Agent

The tint component and the third component comprise a first non-ammonia alkalizing agent and a second non-ammonia alkalizing agent respectively. The first and second non-ammonia alkalizing agents may be the same or different. The non-ammonia alkalizing agent may be an alkanolamine, in particular one selected from monoethanolamine, diethanolamine, triethanolamine, monopropanolamine, dipropanolamine, tripropanolamine, 2-amino-2-methyl-1,3-propanediol, 2-amino-2-methyl-1-propanol (a.k.a. aminomethylpropanol, AMP), 2-amino-2-hydroxymethyl-1,3-propanediol and mixtures thereof. Monoethanolamine (MEA) or aminomethylpropanol (AMP) are commonly used in ammonia-free marketed products and may thus be preferred. Monoethanolamine may be particularly preferred for use as first non-ammonia alkalizing agent and second non-ammonia alkalizing agent.

Although the tint component and/or the third component may comprise in some embodiments some amount of ammonia (for example up to 0.5% by weight of the component) in addition to the non-ammonia alkalizing agent, it may be preferred that the hair coloring composition is free of ammonia. Thus in some embodiments the tint component and the third component do not contain ammonia.

Although the tint component and third component according to the invention may preferably comprise the same non-ammonia alkalizing agent, in particular monoethanolamine, the concentration of the second alkalizing agent in the third component may be higher than the concentration of the first alkalizing agent in the tint component so that the total concentration in non-ammonia alkalizing agent is higher in the ready-to-use coloring composition after the third component has been mixed with the tint component and the oxidizing component.

The concentration in non-ammonia alkalizing agent, in particular MEA, in the third component may be comprised between 3% and 15%, preferably 6% to 12%, more preferably 8% to 10% by weight of the third component, exemplarily 9% and is preferably higher than in the tint component. A relatively high concentration is believed to be necessary to raise the concentration in non-ammonia alkalizing agent in the final composition after mixing. By comparison, the usual concentration in non-ammonia alkalizing agent in a standard tint component for a two-component oxidative coloring composition, as can also be used in the present invention, may be of from 1% to 3% on head, or 1.5% to 5% in the tint component.

Oxidizing Agent

The methods of the invention use an oxidizing component, which comprises an oxidizing agent. The oxidizing component may be any usual oxidizing composition known in the art for this purpose. In particular, the oxidizing component may be an oil-in-water emulsion of hydrogen peroxide ($H_2O_2$). The oxidizing agent may be more generally selected from hydrogen peroxide, sodium periodate, urea peroxide, melamine peroxide, perborates, percarbonates, perphosphates, persilicates, persulphates, peroxidises and mixtures thereof.

The first oxidizing agent may be the same as or different than the second oxidizing agent and is preferably in both cases hydrogen peroxide. The concentration in oxidizing agent may be the same or different in the first and second oxidizing component, however it may be preferred that a higher concentration in oxidizing agent is used in the second oxidizing component in order to maintain a certain concentration on-head.

Usually, in a standard two-component oxidative system, non-ammonia based oxidative hair composition, the concentration in hydrogen peroxide may range from 1% to 3% by weight of the composition. For example, a ColorTouch® hair coloring product from Wella will usually be mixed in 1:2 ratio (by weight) with a 4% or 1.9% $H_2O_2$ emulsion thus resulting in a 2.7% $H_2O_2$, respectively 1.3% concentration on-head.

When a third component is used in one of the steps of the invention, the second oxidizing component may be the same as the first oxidizing component used in the two-component oxidative composition. The oxidizing agent may however be more concentrated in the second oxidizing component than in the first oxidizing component, especially when the relative amount of the oxidizing component in the oxidative composition comprising the third component is lower due to the dilution effect caused by the third component.

The concentration in hydrogen peroxide in the oxidative coloring composition obtained with the third component may be for example from 1% to 6%, in certain embodiments from 2% to 4%, in particular from 2.5 to 3.5%. Using too high concentration of hydrogen peroxide or other oxidizing agent may not provide more lift while being damaging for the hair fiber. The second oxidizing component may comprise hydrogen peroxide as oxidizing agent in a higher concentration than in the first oxidizing component, for example from 3 to 10% by weight of the second oxidizing component, in particular from 6 to 9%.

When the third component is used, the oxidative coloring compositions of the invention may preferably display a weight ratio of alkalizing agent to oxidizing agent (in particular a ratio of non-ammonia alkalizing agent, especially MEA: hydrogen peroxide) which is higher than 1.1, preferably between 1.1 and 4.0, more preferably between 1.2 and 3.0, as this was found to provide a good balance between high lift and acceptable oxidative hair damages.

Formulation Chassis and Other Ingredients

The components provided before mixing into the oxidative coloring compositions of the invention can comprise any usual chassis and use any common ingredients as known in the technical field of coloration, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein derivatives, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

The following are only a few examples, which should be not be considered as limiting, and using other common elements or formulation chassis with the invention is of course possible.

Examples of formulation chassis for the tint component can be found for example in patent literature or adapted from existing commercial products, especially products comprising non-ammonia alkalizing agent such as from the ColorTouch® range marketed by Wella, Inoa® range marketed by L'Oreal or Essensity® range marketed by Schwarzkopf. The components may for example be formulated and delivered as aqueous hair product, emulsion, gel, aerosol, or foam.

A creamy carrier for the tint component or the third component comprising (A) 10 to 30 w. % of at least one fatty alcohol with 10 to 24 carbon atoms; and one or more or all of: (B) 0.2 to 6.0 w. % of at least one diester of formula: $R^1$—CO—O—$(CH_2$—$CH_2$—O$)_n$—CO—$R^2$, where n is 1, 2 or 3, and $R^1$ and $R^2$ are the same or different alkyl radicals with 12 to 20 carbon atoms; (C) 0.5 to 20 w. % glycerine fatty acid ester with 10 to 24 carbon atoms; (D) 0.1 to 10 w. % of non-ionic and/or anionic and/or ampholytic emulsifiers, in relation to the total weight of this tint component, and (E) has a pH of 4.5 to 12.5, may be used, as is for example disclosed in EP594,811A1. Lower level of fatty alcohol can also be used in this chassis if a less thick composition is desired, for example level of from 2% of at least one fatty alcohol with 10 to 24 carbon atoms.

The formulations disclosed in WO98/11863A2 may also be used. The formulations disclosed in this document contain a beeswax-protein hydrolysate- and/or amino acid association, which however may or may be not present in the tint component of the present invention.

The invention may also be put in practice with a three-component system, for example as disclosed in L'Oreal's US2010/0223739A2, in which case the aqueous cosmetic composition (A) comprising at least one fatty substance and at least one surfactant as defined in this document may be considered as a fourth composition.

The oxidizing component and the third component may be based on the same or similar (i.e. having the same ingredients but possibly at different level) formulation chassis as the tint component, but these components are normally free of oxidative dye precursors or direct dyes.

Among the usual ingredients encountered in coloring compositions, the presence of a chelant such as EDTA or EDDS may be beneficial in several ways, as it was shown that chelants can reduce hair damage due to the oxidizing agent (see WO02/089754, in particular the chelants listed on page 14 line 26 to page 17 line 5). Chelants, usually disodium EDTA, are also commonly used as stabilizer in water-containing oxidizing component.

Among primary dyes, common primary intermediates are for example toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-didhydroxyethyl)-p-phenylenediamine, 2-chloro-p-phenylenediamine, p-aminophenol, p-methylaminophenol, 4-amino-m-cresol, 6-amino-m-cresol, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate.

Commonly used couplers are for example resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylamino-phenol, 3-amino-2,6-dimethylphenol, 3-amino-2,4-dichlorphenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylamino-anisole, 1,3-bis-(2,4-diaminophenoxy)-propane, 2,6-dihydroxyethylamino-toluene, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol, 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline). These and other primary intermediates and couplers may be used in different combination to achieve the nuance sought, as is known in the art.

Direct dyes may also be incorporated in any of components of the invention, in particular the tint component. A list of exemplary suitable direct dyes is indicated on page 3 line 9 to page 9 line 24. The following direct dyes are commonly used: Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methyl-morpholin-4-ium-methylsulfate, (E)-1-(2-(4-(4,5-dimethylthiazol-2-yl)diazenyl)phenyl)(ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

The coloring compositions of the invention and any of the components used in the invention may comprise a thickener, in particular a polymeric thickener in an amount sufficient to provide the composition with a viscosity so that it can be readily applied to the hair without unduly dripping off the hair, as is known in the art. Typically, such an amount will be at least about 0.1%, in some embodiments, at least about 0.5%, in other embodiments, at least about 1%, by weight of the composition. Examples of commonly used associative polymeric thickeners are sold under the tradename Aculy-22 by the company Rohm & Haas, Permulen TR1, Carbopol 2020, Carbopol Ultrez-21 by the company Noveon, and Structure 2001 and Structure 3001 by the company National Starch. Other suitable polymers include polyether polyurethanes, for example Aculyn-44 and Aculyn-46 by the company Rohm and Haas. Another suitable associative polymer is cellulose modified with groups comprising at least one C8-C30 fatty chain, such as the product Natrosol Plus Grade 330 CS sold by the company Aqualon.

Suitable non-associative cross-linked polycarboxylic polymers for use herein can be chosen, for example, from: (i) cross-linked acrylic acid homopolymers; or (ii) copolymers of acrylic or (meth)acrylic acid and of C1-C6 alkyl acrylate or (meth)acrylate. Such polymers are sold under the names Carbopol 980, 981, 954, 2984, 5984 by the company Noveon or Synthalen M, Synthalen L and Synthalen K by the company 3V Sigma, or Aculyn-33 by the company Rohm and Haas.

Polysaccharides may also be used, for example, glucans, modified and unmodified starches, amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc.

Salt tolerant thickeners may also be advantageously used, including but not limited to: xanthan, guar, hydroxypropyl guar, scleroglucan, methyl cellulose, ethyl cellulose (available as AQUACOTE®, hydroxyethyl cellulose (NATROSOL®), carboxymethyl cellulose, hydroxypropylmethyl cellulose, microcrystalline cellulose, hydroxybutylmethyl cellulose, hydroxypropyl cellulose (available as KLUCEL®), hydroxyethyl ethyl cellulose, cetyl hydroxyethyl cellulose (available as NATROSOL® Plus 330), N-vinylpyrollidone (available as POVIDONE®), Acrylates/Ceteth-20 Itaconate Copolymer (available as STRUCTURE® 3001), hydroxypropyl starch phosphate (available as STRUCTURE® ZEA), polyethoxylated urethanes or polycarbamyl polyglycol ester (e.g. PEG-150/Decyl/SMDI copolymer (e.g. ACULYN® 44), PEG-150/Stearyl/SMDI copolymer (available as ACULYN® 46), trihydroxystearin (available as THIXCIN®), acrylates copolymer (e.g. available as ACULYN® 33) or hydrophobically modified acrylate copolymers (e.g. Acrylates/Steareth-20 Methacrylate Copolymer (available as ACULYN® 22), acrylates/steareth-20 methacrylate crosspolymer (available as ACULYN® 88), acrylates/vinyl neodecanoate crosspolymer (available as ACULYN® 38), acrylates/beheneth-25 methacrylate copolymer (available as ACULYN® 28), acrylates/C10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain, and blends of Ceteth-10 phosphate, Di-cetyl phosphate and Cetearyl alcohol (available as CRODAFOS® CES).

The components of the invention can be manufactured using any suitable standard processes known in the art.

Mixing

The different components may be mixed together in any order. When three components have to be mixed, they may be all mixed together or one after the other. For example the tint component and the oxidizing component may be mixed together, and the third component then added to this intermediate mixture.

A mixing ratio of 1:1:1 (by weight) for each component may be advantageous when a third component is used in one of the steps of the invention. This 1:1:1 ratio allows the user to dose the different component in a simple way, as well as allow a simple calculation of the concentration of the oxidizing agent on-head. A concentration of 3% hydrogen peroxide on-head can for example be thus obtained by using a 9% concentrated hydrogen peroxide oxidizing component.

Packaging

Before use, the different components used in the invention are normally packaged separately from one another. The components may be packaged separate primary packages such as plastic bottle or sachet. The components, in particular each component of a two-component composition, may however be packaged separately but within a common secondary package such as a carton or in different compartment of an aerosol or foam bottle, as in known in the trade. A conditioning composition, which can be applied after rinsing of the hair coloring composition, may also be packaged in such secondary package. On the other hand, the different components of the invention, in particular the third component, may be sold separately from the other components.

Application to the Hair

Application of the hair coloring composition to the hair may be undertaken in several ways. Application of the hair coloring composition may take place on the whole head of hair of an end user. As used herein, the "whole head of hair" means that the hair all over the head from the root of the hair to the tip of the hair is included in the application process. By contrast, the application of the hair coloring composition may take place on the root portion of the hair. The application to the root portion of the hair may still be over the entire head of the end user, but application of the hair coloring composition is applied only to the section of hair closest to the head (root portion), which is between about 0.01 mm to about 4 mm from the scalp of the head. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in an additional container. In the latter case, the conditioner can be mixed immediately before use and applied together with the other components, or the content of the additional container can be applied (after an optional rinse step) as a post-treatment immediately after the hair coloring composition.

According to one method for oxidatively coloring hair, the method comprises mixing a tint component and an oxidizing component and optionally a third component comprising a second non-ammonia alkalizing agent together to form a hair coloring composition, applying the hair coloring composition to the hair to form a treated hair surface, waiting for a period of 5-45 minutes, such as 20-30 minutes, and then removing the hair coloring composition from the treated hair surface.

The methods of coloring hair also may further comprise working the hair coloring composition into the treated hair surface by hand or by a tool for a few minutes to ensure uniform application to the entire treated hair surface. The hair coloring composition remains on the treated hair surface while the end hair color develops for a time period of 5 to 45 minutes to form oxidatively colored hair. The consumer then rinses his/her oxidatively colored hair thoroughly with tap water and allows it to dry and/or styles the oxidatively colored hair.

EXAMPLES

The following examples demonstrate the advantages of the present invention. The following abbreviations are used for the different components:

CT: ColorTouch® (a "Level 2" coloring composition with MEA as alkalizing agent) in particular the shade 10/0 and 7/3 ("CT10/0" and "CT7/3" respectively). The INCI list and percentage weight range for CT10/0 are: (>10%:) Aqua, (1%-10%:) Cetearyl Alcohol, Ethanolamine, Sodium Sulfate, Laureth-3, Sodium Laureth Sulfate, Glyceryl Stearate SE, (0.1%-1%:) Decyltetradecanol, Sodium Lauryl Sulfate, Cera Alba, Parfum, Sodium Cocoyl Isethionate, Mica, Sodium Sulfite, Ascorbic Acid, Etidronic acid, Hydrolyzed Keratin, (<0.1%:) Colorant, Citric acid.

The INCI list and percentage weight range for CT7/3 are: (>10%:) Aqua; (1%-10%:) Cetearyl Alcohol, Ethanolamine, Sodium Sulfate, Laureth-3, Sodium Laureth Sulfate, Sodium Sulfate, Glyceryl Stearate SE; (0.1%-1%:) Decyltetradecanol, Sodium Lauryl Sulfate, Toluene-2,5-Diamine Sulfate, Cera Alba, Parfum, Sodium Cocoyl Isethionate, Mica, Sodium Sulfite, 2-Methylresorcinol, Ascorbic Acid, Hydrolyzed Keratin; (<0.1%) Colorant, m-Aminophenol, 2-Amino-6-Chloro-4-Nitrophenol, Resorcinol, Citric acid.

4% CT Emulsion: ColorTouch® Oxidizing Emulsion having 4% $H_2O_2$ concentration. The INCI list and percentage weight range for 4% CT Emulsion are (>10%:) Aqua, (1%-10%:) Hydrogen Peroxide, Cetearyl Alcohol, (0.1%-1%:) Lanolin Alcohol, Sodium Lauryl Sulfate, Parfum, Salicylic Acid, (<0.1%:) Disodium Phosphate, Phosphoric Acid, Etidronic Acid, Potassium Phosphate, Tocopherol.

6%, 9% Welloxon: Welloxon® Emulsion with respectively 6 and 9 w. % $H_2O_2$, comprising as INCI ingredients; Aqua, Hydrogen Peroxide, Cetearyl Alcohol, Ceteareth-25, Salicylic Acid, Phosphoric Acid, Disodium Phosphate, Etidronic Acid.

KP10/0: Koleston Perfect 10/0 (a "Level 3" lightening component with ammonia as alkalizing agent). The INCI list and percentage weight range for KP10/0 are (>10%:) Aqua, Cetearyl Alcohol, (1-10%:) Glyceryl Stearate SE, Ammonium Hydroxide, Sodium Laureth Sulfate, Lanolin Alcohol, Sodium Lauryl Sulfate, Sodium Sulfate, Glycol Distearate, Sodium Cocoyl Isethionate, Sodium sulfite, Ascorbic Acid, Parfum, (<0.1%:), Disodium EDTA, Toluene-2,5-Diamine Sulfate, 2-Methylresorcinol, Citric Acid, Resorcinol, Tocopherol.

All these components are marketed products from Wella, a German subsidiary of the Procter & Gamble Company.

The third component ("Booster") according to the invention was an O/W emulsion with the following formula:

TABLE 1

| Ingredient | Percent |
| --- | --- |
| Ethanolamine | 9 |
| Cetearyl Alcohol (and) Sodium Lauryl Sulfate (90:10 ratio) | 7 |
| Sodium Sulfite | 4 |
| Laureth-3 | 3 |
| Glyceral Distearate SE | 2.2 |
| Decyltetradecanol | 0.8 |
| Beeswax | 0.5 |
| Perfume | 0.5 |
| Gleamer Flake | 0.5 |
| Sodium cocoyl isothianate | 0.2 |
| Water | q.s. |

In the following experiment, the CT tint component was mixed in a 1:2 weight ratio with the oxidizing component if the Booster was not used (two-component mix). The KP tint component was mixed in a 1:1 ratio with the oxidizing component to reflect usual practice. If the Booster was used to make a three-components mix, then each component was mixed in a 1:1:1 ratio.

In a first set of experiment, the shade 10/0 (natural bright blond) was used for both KP and CT. After mixing, the resulting lightening compositions were applied on tresses of medium brown hair 1.4 cm wide, 13 cm long with a development time of 35 mn on a ratio of 4 gram composition for 1 gram of hair. The hair was then shampooed and conditioned with standard products. The amount of lift obtained was then measured using a Konica/Minolta D 508 Colorimeter and characterized by the difference in L* value measured. The results and the composition's concentration in MEA and $H_2O_2$ are summarized in the Table below.

TABLE 2

| Composition tested | Mixing ratio of the components | ΔL* measured | w. % of MEA in the composition | w. % $H_2O_2$ in the composition |
| --- | --- | --- | --- | --- |
| CT10/0 + 4% CT Emulsion | 1:2 | 1.16 | 1.33 | 2.7 |
| CT10/0 + Booster + 4% CT Emulsion | 1:1:1 | 2.95 | 4.33 | 1.33 |
| CT10/0 + 6% Welloxon | 1:2 | 1.42 | 1.33 | 4 |
| CT10/0 + Booster + 6% Welloxon | 1:1:1 | 3.60 | 4.33 | 2 |
| CT10/0 + Booster + 9% Welloxon | 1:1:1 | 4.85 | 4.33 | 3 |
| CT10/0 + Booster + 12% Welloxon | 1:1:1 | 4.72 | 4.33 | 4 |
| KP10/0 + 9% Welloxon | 1:1 | 4.18 | — | 4.5 |
| KP10/0 + 12% Welloxon | 1:1 | 5.97 | — | 6 |

This experiment shows that the third component ("Booster") can significantly increase the level of lift provided by a hair coloring composition comprising a non-ammonia alkalizing agent. For example comparing the first two compositions of the table, the lift (ΔL*) went from 1.16 for a composition without the Booster to 2.95 for a composition with the Booster using the same tint and oxidizing components (CT10/0 and 4% CT Emulsion). Surprisingly, the amount of lift went up even as the concentration in peroxide was roughly halved. Although not wishing to be bound by theory, the inventors hypothesize that this surprising effect is caused by the raised level of non-ammonia alkalizing agent (MEA).

The results are even more striking when an oxidizing agent is used in a more concentrated form in the three component system, as the lift can then be even higher, e.g. 3.60 with a 6% concentrated $H_2O_2$ component (2% $H_2O_2$ on-head) or 4.85 with a 9% concentrated $H_2O_2$ component (3% on-head), and approaches or overtakes the performance of a marketed Level 3 product (KP+9% Welloxon). However increasing the level of peroxide in the oxidizing component to 12% when the third component is used did not lead to more lift, as a plateau seems to be reached.

The table 2 above showed that the lift can be improved when using a third component of the present invention. The inventors have further found that there was little "color shift" between the coloring compositions obtained by mixing two components compared to when three components according to the invention are mixed. This was surprising for the inventors, as it was expected that changing the concentration in alkalizing agent and oxidizing agent would significantly change the tonality of the end result. Change of tonality, or "color shift" can be measured by comparing a*, b* values, preferably measured on natural white hair to eliminate the influence of the natural melanin. It is generally considered that there is no significant color lift when both Δa* and Δb* values are of less than 2.

The following table shows the measured Δa* and Δb* values after a coloration with and without the third component. The shade of CT used was 7/3 (medium blond). Natural white hair were treated as indicated above and the a*, b* values measured. Hair colored with CT7/3+4% CT Emulsion was taken as reference and the Δa* and Δb* values calculated using this reference.

TABLE 3

| Composition tested | Δa* | Δb* |
|---|---|---|
| CT7/3 + 6% Welloxon + Booster | 0.20 | 0.77 |
| CT7/3 + 9% Welloxon + Booster | 0.29 | 0.39 |

This experiment shows that the third component had little impact on the tonality obtained on white natural hair. This is particularly useful as it shows that existing two-component composition (e.g. Level 2) can have their lift power increased by the third component ("Booster") without a significant impact on the tonality.

Remark

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

"While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an oxidative hair coloring composition, said method comprising the steps of:
   providing a tint component and an oxidizing component, said tint component comprising a first non-ammonia alkalizing agent and oxidative primary dyes, and
   mixing the tint component and the oxidizing component with a third component comprising a second non-ammonia alkalizing agent to make the oxidative hair coloring composition.

2. A method according to claim 1 wherein the oxidizing component comprises from 6 to 9 percent of hydrogen peroxide by weight of the oxidizing component.

3. A method according to claim 1 wherein the tint component, the oxidizing component and the third component are mixed in a 1:1:1 weight ratio.

4. A method according to claim 1 wherein the concentration of the second non-ammonia alkalizing agent in the third component is higher than the concentration of the first non-ammonia alkalizing agent in the tint component.

5. A method according to claim 4 wherein the tint component and the third component are free of ammonia.

6. A method according to claim 1 wherein the third component does not comprise oxidative dye precursors.

7. A method according to claim 1 wherein the weight ratio of alkalizing agent to oxidizing agent in the oxidative hair coloring composition obtained by mixing the tint, oxidizing and third components is higher than 1.1.

8. A method according to the claim 7, wherein the oxidative hair coloring composition further comprises less than or equal to 3.0 by weight percent oxidizing agent.

9. A method for making at the discretion of the user either a first oxidative hair coloring composition or a second oxidative hair coloring composition, said second oxidative hair coloring composition having a relatively higher lift than said first oxidative hair coloring composition, said method comprising the steps of:
   providing a tint component comprising a first non-ammonia alkalizing agent and oxidative primary dyes, and
   mixing the tint component with a first oxidizing component to obtain the first hair coloring composition; or
   providing a third component comprising a second non-ammonia alkalizing agent, and mixing the tint component with a second oxidizing component and the third component to obtain a second hair coloring composition having a relatively higher lift than the first coloring composition.

10. A method according to claim 9 wherein the concentration of the second non-ammonia alkalizing agent in the third component is higher than the concentration of the first non-ammonia alkalizing agent in the tint component.

11. A method according to claim 9 wherein the tint component and the third component are free of ammonia.

12. A method according to claim 9 wherein the first oxidizing component and the second oxidizing component both comprise hydrogen peroxide as an oxidizing agent.

13. A method according to claim 9 wherein the second oxidizing component has a higher concentration of oxidizing agent than the first oxidizing component.

14. A method according to claim 9 wherein the third component does not comprise oxidative dye precursors.

15. A method according to claim 9 wherein the tint component is mixed with the first oxidizing component in a 1:1 weight ratio to obtain the first hair coloring composition, and wherein the tint component, the second oxidizing component and the third component are mixed in a 1:1:1 weight ratio to obtain the second hair coloring composition.

16. A method according to claim 9 wherein the weight ratio of alkalizing agent to oxidizing agent in the second oxidative coloring composition is higher than 1.1.

17. A method according to claim 16, wherein said second oxidative coloring composition further comprises less than or equal to 3.0 by weight percent oxidizing agent.

\* \* \* \* \*